United States Patent
Hoyle, Jr.

(10) Patent No.: US 7,470,259 B2
(45) Date of Patent: Dec. 30, 2008

(54) DOSAGE CONTROL SYRINGE

(76) Inventor: John D. Hoyle, Jr., 7719 Forest Ct., NE., Rockford, MI (US) 49341

( * ) Notice: Subject to any disclaimer, the term of this patent is extended or adjusted under 35 U.S.C. 154(b) by 63 days.

(21) Appl. No.: 11/277,431

(22) Filed: Mar. 24, 2006

(65) Prior Publication Data

US 2007/0225656 A1    Sep. 27, 2007

(51) Int. Cl.
*A61M 5/00*  (2006.01)
*A61M 5/178* (2006.01)
*A61M 3/00*  (2006.01)

(52) U.S. Cl. .................. 604/207; 604/186; 604/189; 604/208; 604/209

(58) Field of Classification Search .......... 604/500, 604/506, 520, 82, 86–88, 181, 186, 187, 604/189, 200, 201, 203, 206–210, 218, 232, 604/241
See application file for complete search history.

(56) References Cited

U.S. PATENT DOCUMENTS

| | | | |
|---|---|---|---|
| 2,369,304 A | 2/1945 | Lewis | |
| 2,856,925 A | 10/1958 | Helmer et al. | |
| 3,563,240 A | 2/1971 | Silver | |
| 4,275,729 A | 6/1981 | Silver et al. | |
| 4,444,335 A | 4/1984 | Wood et al. | |
| 4,654,035 A | 3/1987 | Ando | |
| RE32,974 E | 7/1989 | Porat et al. | |
| 4,874,385 A | 10/1989 | Moran et al. | |
| 4,950,163 A | 8/1990 | Zimble | |
| 5,139,484 A | 8/1992 | Hazon et al. | |
| 5,215,536 A | 6/1993 | Lampropoulos et al. | |
| 5,281,198 A * | 1/1994 | Haber et al. | 604/86 |
| 5,328,486 A | 7/1994 | Woodruff | |
| 5,344,409 A | 9/1994 | Ennis, III et al. | |
| 5,380,295 A | 1/1995 | Vacca | |
| 5,382,241 A | 1/1995 | Choudhury et al. | |
| 5,531,708 A | 7/1996 | Woodruff | |
| 5,685,864 A * | 11/1997 | Shanley et al. | 604/211 |
| 5,807,346 A | 9/1998 | Frezza | |
| 5,961,495 A * | 10/1999 | Walters et al. | 604/208 |
| 6,283,941 B1 | 9/2001 | Schoenfeld | |
| 6,368,308 B1 | 4/2002 | Nerney | |
| 6,413,241 B1 | 7/2002 | Slishman | |
| 6,569,115 B1 * | 5/2003 | Barker et al. | 604/110 |
| 2001/0009990 A1 | 7/2001 | Hostettler et al. | |
| 2001/0051792 A1 | 12/2001 | Kirchhofer et al. | |
| 2002/0010429 A1 | 1/2002 | Grogan, Jr. | |
| 2002/0087121 A1 | 7/2002 | Slishman | |
| 2004/0162528 A1* | 8/2004 | Horvath et al. | 604/207 |

* cited by examiner

*Primary Examiner*—Kevin C Sirmons
*Assistant Examiner*—Bhisma Mehta
(74) *Attorney, Agent, or Firm*—Warner Norcross & Judd LLP

(57) ABSTRACT

A syringe is provided for limiting the dosage of medication delivered to a patient to a pre-determined amount. The syringe assembly includes an injector assembly and vial of medication. The injector assembly has an adjustable dosage control which rides in a track on the injector assembly for limiting vial movement. Once an appropriate dosage is selected using the dosage control, the vial is engaged with the injector assembly. As the vial is pressured into the injector assembly medication is forced through the needle. Once the vial reaches the dosage control, vial movement is obstructed and dosage effectively limited.

16 Claims, 8 Drawing Sheets

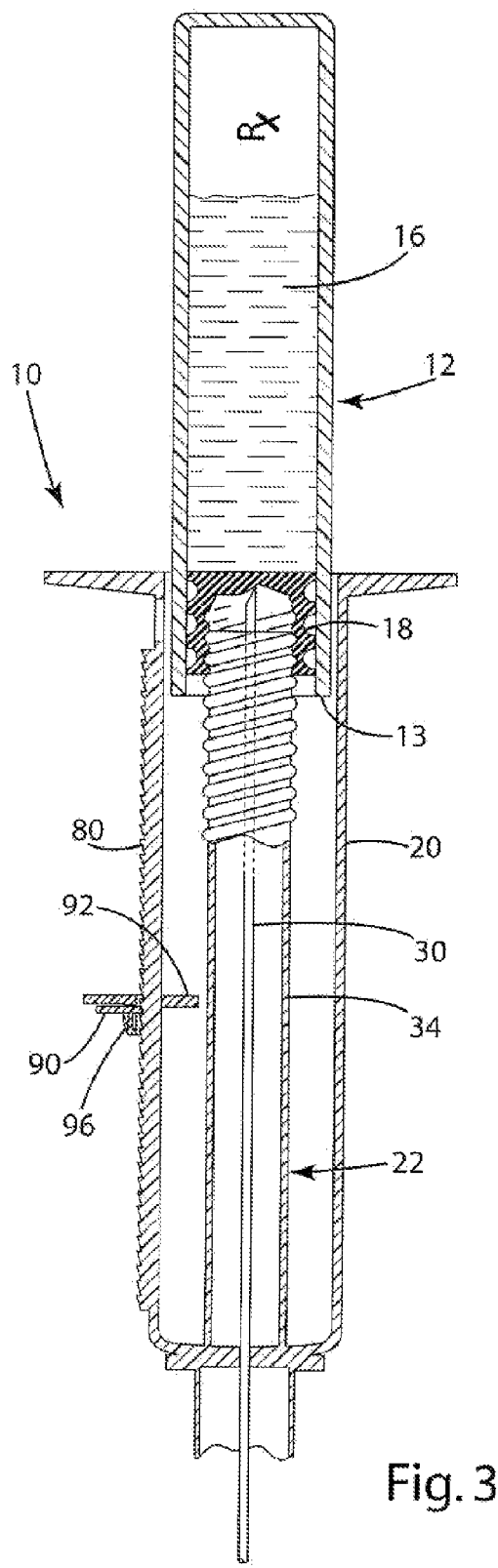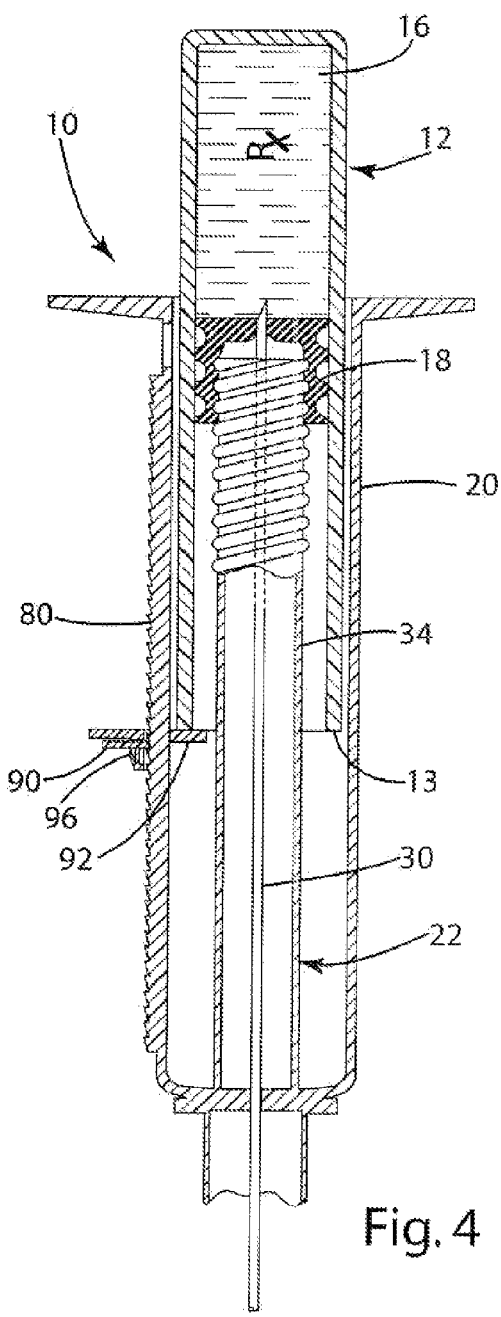

DOSAGE CONTROL SYRINGE

BACKGROUND OF THE INVENTION

The present invention relates to syringes, and more particularly to vial syringes capable of limiting the dosage dispensed to a predetermined amount.

The medical community is constantly striving to reduce errors wherever possible. One area of particular concern is controlling the amount of dosage administered to medical patients, particularly in emergency or high stress situations. Some studies have shown that incorrect dosages of emergency resuscitation drugs are mistakenly given in an emergency setting more than 40% of the time.

Some medical errors occur because of dosage miscalculation or dosage administration. Known medication packaging requires multiple calculations be made in order to deliver an appropriate dose. While these conversions are not necessarily complicated, they can be tedious and/or difficult to calculate in high pressure environments, such as an emergency department. An error in dosage calculation can have devastating consequences.

Some syringes are designed to reduce dosage miscalculation by labeling the syringe barrel with non-volumetric measuring indicia to eliminate weight to dosage conversions. An example of one such construction is shown in U.S. patent application Ser. No. 10/074,009 to Slishman. This construction only helps to reduce dosage miscalculation and does nothing to help reduce dosage administration errors. That is, the syringe operator is still burdened with the requirement of watching the graduations on the container as an appropriate amount of medication is drawn into the syringes. In some syringes, the container is funnel shaped, meaning the rate of withdrawal of the medication will change as more volume is withdrawn, increasing the time to withdraw appropriate amount of medication and risking and overshoot and withdrawing too much.

Other syringes are aimed specifically to reduce errors in dosage administration. Examples of such syringes includes U.S. Pat. No. 4,444,335 to Wood, U.S. Pat. No. 4,874,385 to Moran, and U.S. Pat. No. 4,654,035 to Ando. Each of these constructions use a mechanical stopping element attached to the syringe plunger to physically limit syringe plunger movement and thereby control dosage.

Each of the syringes discussed above requires the user to draw medication into the syringe before it can be dispensed. In some syringes, pre-filled vials replace the syringe plunger and obviate the need to draw medication into the syringe. This can be especially valuable in time sensitive situations such as an emergency department. The vial syringe works by inserting a vial into an injector and rotating the vial clockwise a specific number of turns, medication enters the injector needle, whereupon the injector is uncapped and ready for use. An example of one such construction is the Abboject syringe manufactured by Abbott Laboratories. Some vial syringes use vials that contain one adult dosage, so there is little possibility of dosage miscalculation or dosage administration error. Unfortunately, sometimes a one size fits all dosage is not appropriate. Specifically, some resuscitation drugs are packaged for adults which results in potential error when a smaller dose must be delivered to a child. That is, at times, less than or more than a single adult dose may have to be administered.

Some vial syringes use vials which contain multiple dosages and rely on the user to judge the amount injected using graduations on the syringe barrel. Although the user saves time not having to draw the medication, multi-dose vial syringes still require the user to watch graduations on the barrel so as not to under or overdose. Unfortunately, a vial syringe does not have a plunger, hence the mechanical stopping elements described in the patents above are unhelpful.

Previous devices fail to meet the needs of the medical community for error reduction. In the high pressure situation of a patient in cardiac arrest or near death, especially a pediatric patient, it is too easy to administer an incorrect dosage using known syringe constructions.

SUMMARY OF THE INVENTION

The aforementioned problems are addressed by the present invention wherein a syringe is configured with a moveable locking dosage control to assist in providing an appropriate dosage of medication to the patient.

In one embodiment, the syringe includes a syringe barrel, a needle or needle assembly mounted in the barrel, a vial of medication closed with a stopper for engaging the needle, a track disposed on the syringe, and an adjustable dosage control which rides in the track for limiting vial movement within the barrel.

The syringe barrel may include indicia or graduations. The indicia or graduations correspond directly to dosages or to a dosage indicative characteristic. The control may include an indicator for use with the indicia or graduations. The dosage control and indicator are movable and lockable such that the dosage indicator selects a particular dosage or dosage indicative characteristic.

The dosage control syringe may be operated by moving the dosage control to select an appropriate dosage, engaging a vial of medication with the needle assembly of the syringe barrel, and pushing the vial of medication into the syringe barrel until the vial engages the dosage control thereby administering the selected dosage.

The present invention provides a syringe that addresses the needs of the medical community for error reduction. The dosage control is easily and quickly actuated. This is important in emergency situations where time may be at a premium. The dosage control facilitates accurate dosage even in high stress situations, such as an emergency department, by limiting the dosage capable of being administered. The dosage control is a positive mechanical stop that alleviates the operator from having to closely watch the graduations on the syringe barrel and thereby assists in preventing under-dosing or over-dosing without monopolizing valuable time. The current device also serves as a quality assurance tool in that the dose given to the patient can be visually confirmed after it has been administered.

These and other objects, advantages, and features of the invention will be readily understood and appreciated by reference to the detailed description of the current embodiment and the drawings.

BRIEF DESCRIPTION OF THE DRAWINGS

FIG. 3 is a sectional side view of the vial assembly initially engaging a needle of the injector assembly.

FIG. 4 is a sectional side view of the vial assembly engaging an obstruction within the injector assembly.

DESCRIPTION OF THE CURRENT EMBODIMENT

Figure 1:
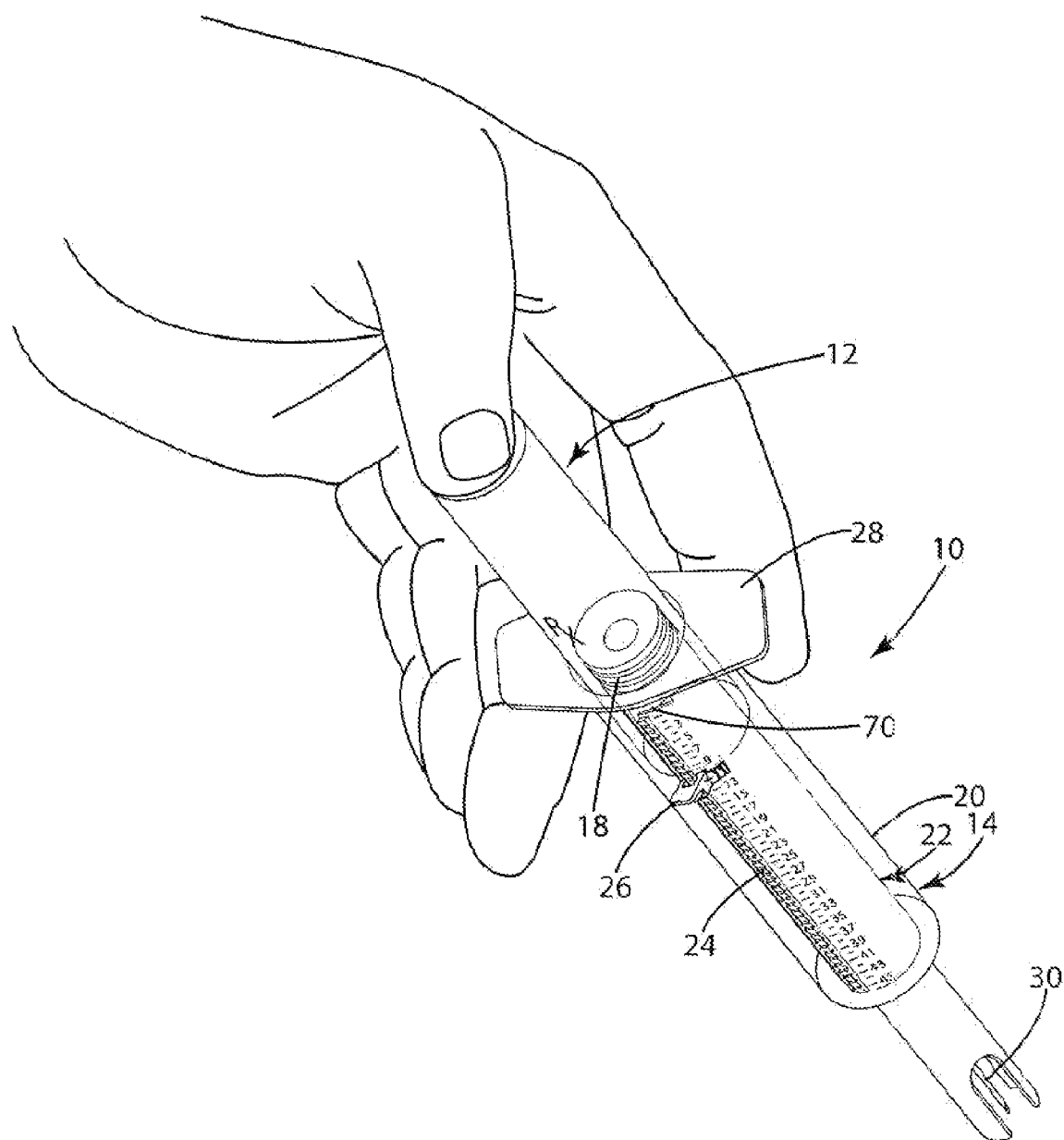
FIG. 1 is a perspective view of one embodiment of a dosage control syringe in use.
Figure 2:
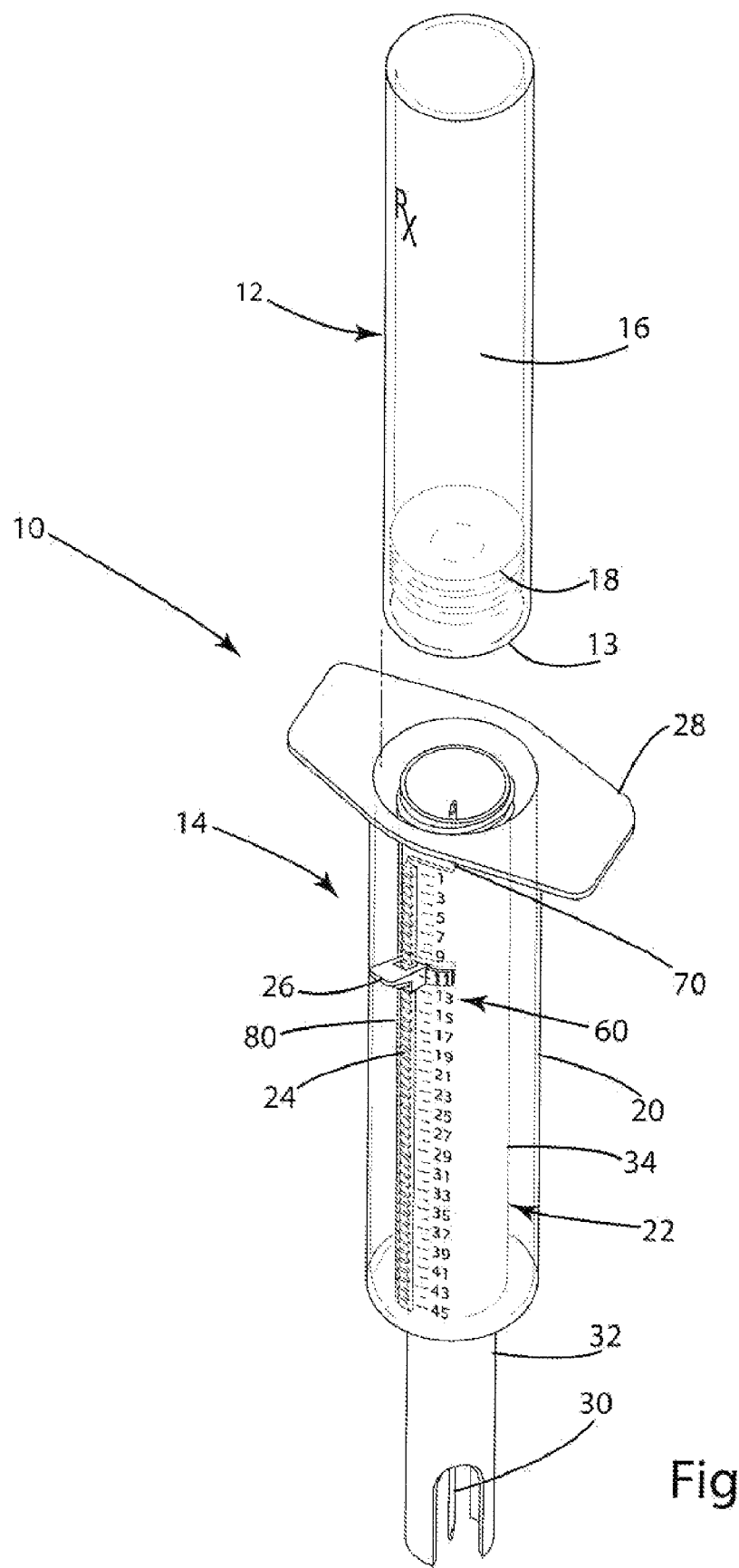
FIG. 2 is a perspective view of a vial assembly and an injector assembly of the dosage control syringe.

The present invention provides a dosage control syringe for administering an appropriate dosage of medication to a patient. A dosage control syringe constructed in accordance with one embodiment of the invention is illustrated in FIGS. 1-5 and generally designated 10. As perhaps best shown in FIG. 2, the syringe 10 generally includes a vial 12 and an injector assembly 14. The vial 12 is filled with medication 16 and sealed with a stopper 18. The injector assembly 14 generally includes a syringe barrel 20, a needle assembly 22, a track 24, and a dosage control 26. In use, the dosage control 26 is selectively locked into a position on the track 24 by a user to selectively limit vial 12 movement within the syringe barrel 20 and therefore selectively limit the amount of medication delivered from the vial 12 through the needle assembly 22 to the patient. The present invention is described in connection with a vial syringe having a vial 12 and vial injector assembly 14.

The vial 12 is a generally cylindrical glass container (calibrated or un-calibrated) with one open end formed by a vial edge 13. The size, shape, and composition of the vial may vary from application to application. The vial 12 may be filled with one or more than one of many suitable medical solutions. In one embodiment, the vial is prominently labeled (not shown) with specific drug and dosage indicia.

The filled vial 12 is generally sealed with a slidable elastomeric or rubber stopper 18. Other suitable vial closures may be implemented in accordance with other embodiments of the present invention. The stopper 18 is at least partially threaded to facilitate engagement with the needle assembly 22, shown in FIG. 3. Although the stopper 18 of the illustrated embodiments is made from elastomeric material, the composition of the stopper need not be so limited. Any material having the appropriate frictional and penetrable properties may be utilized.

The general components of the injector assembly 14 are illustrated in FIG. 1-4. The injector assembly 14 generally includes a syringe barrel 20, a needle assembly 22 at least partially mounted within the syringe barrel 20, a track 24 mounted on (or integral with) the injector assembly 14, and a dosage control 26 movable along the track 24. Additional or equivalent components may be easily incorporated into the present invention. For example, wings 28 may be connected to or formed at an end of the syringe barrel 20 which extend substantially perpendicular to the syringe barrel 20. The wings may be made of the same or different material than the syringe barrel 14. The wings may assist in the grip and operation of the syringe.

The syringe barrel 20 is a generally elongated, rigid, and hollow cylinder typically constructed of a moldable thermoplastic such as medical grade polypropylene. The distal end of the syringe barrel 20 is generally open and has a diameter large enough to facilitate the vial 12 sliding within the barrel. The proximal end of the syringe barrel 20 is substantially closed. The size, shape, and composition of the syringe barrel may vary, the present invention can easily be incorporated into alternative syringe housings. For example, in one embodiment the syringe housing is glass instead of plastic.

The elongated surface of the syringe barrel 20 includes a hole (or aperture) 70 and a slot 42. The hole 70 is large enough to provide the dosage control 26 initial access to the barrel interior. The placement of the slot 42 allows the dosage control to ride along the track 24 as will be discussed in more detail below.

The syringe barrel 20 may be labeled with dosage markings 60 corresponding with various dosage control positions on the track 24. The markings may correspond directly to dosages or to dosage indicative characteristics. The markings 60 of the illustrated embodiments are weight-based graduations, which are shown in kilograms and run from 3 kg to 45 kg in 2 kilogram graduations. The unit type amount of graduations may vary as desired. Although the markings in the illustrated embodiment occur in a straight line along the length of the barrel, they may be alternatively configured. For example, the markings may be staggered along both sides of the track 24 to allow more space for each individual marking. Further, additional or fewer markings are contemplated. It may be desirable to include additional markings between the smaller dosages because any over-dosing or under-dosing at those dosages may have a bigger impact. Although the illustrated embodiment shows the graduations evenly spaced in a linear fashion along the tube, an alternative embodiment may use graduations spaced in a non-linear fashion. In one embodiment, the syringe barrel 20 is prominently labeled with specific drug information it is to be used for.

The needle assembly 22 is coaxially mounted within the syringe barrel 20 and extends from the distal end of the syringe barrel 20, along the length of the barrel, and engages the closed proximal end of the syringe barrel 20. The needle assembly 22 includes an integral injector needle 30, a mounting hub 32, and a support structure 34. Various suitable needle assemblies are generally known and therefore will not be described in detail.

The needle 30 provides a delivery mechanism for the medication to reach the patient. In one embodiment, the needle 30 is an integral, forward extending sharp delivery needle that can be used to inject medical solution directly or indirectly into a patient. A removable needle cover (not shown) may protect against accidental needle stick and prevent the sterile needle from contamination prior to use.

Generally, the needle 30 has a distal end for interfacing with the stopper 18 and a proximal end with a sharpened tip mounted to the proximal end of the syringe barrel 20 at a mounting hub 32. A removable cap (not shown) may close the distal end of the syringe barrel 20 until the vial, 12 is matingly attached. The support structure 34 generally sheaths the needle 30 within the syringe barrel 20 and provides a threadable engagement with the stopper 18 such that the needle 30 penetrates the stopper causing fluid communication between the vial 12 and the needle assembly 22. Although the illustrated embodiments show a threaded engagement between the stopper 18 and support structure 34, alternative suitable mating interfaces between the stopper 18 and the support structure 34 are contemplated. Threads for stopper 18 and support structure 34 may be drug specific. That is, in the drug specific thread embodiment, a vial of a particular drug will not mate with a syringe barrel for a different drug, and vice versa. This reduces the chance of an incorrect vial being mated to a drug-specific syringe barrel.

Generally, the track 24 includes a guide 82 and a locking mechanism 80. In one embodiment, the track 24 is disposed on the injector assembly 14. In the depicted embodiment the track 24 is integrally formed with the syringe barrel 20, alternatively the track 24 may be mounted on the syringe barrel 20. In another embodiment, part or all of the track 24 may be disposed on the support structure 34.

Figure 5:
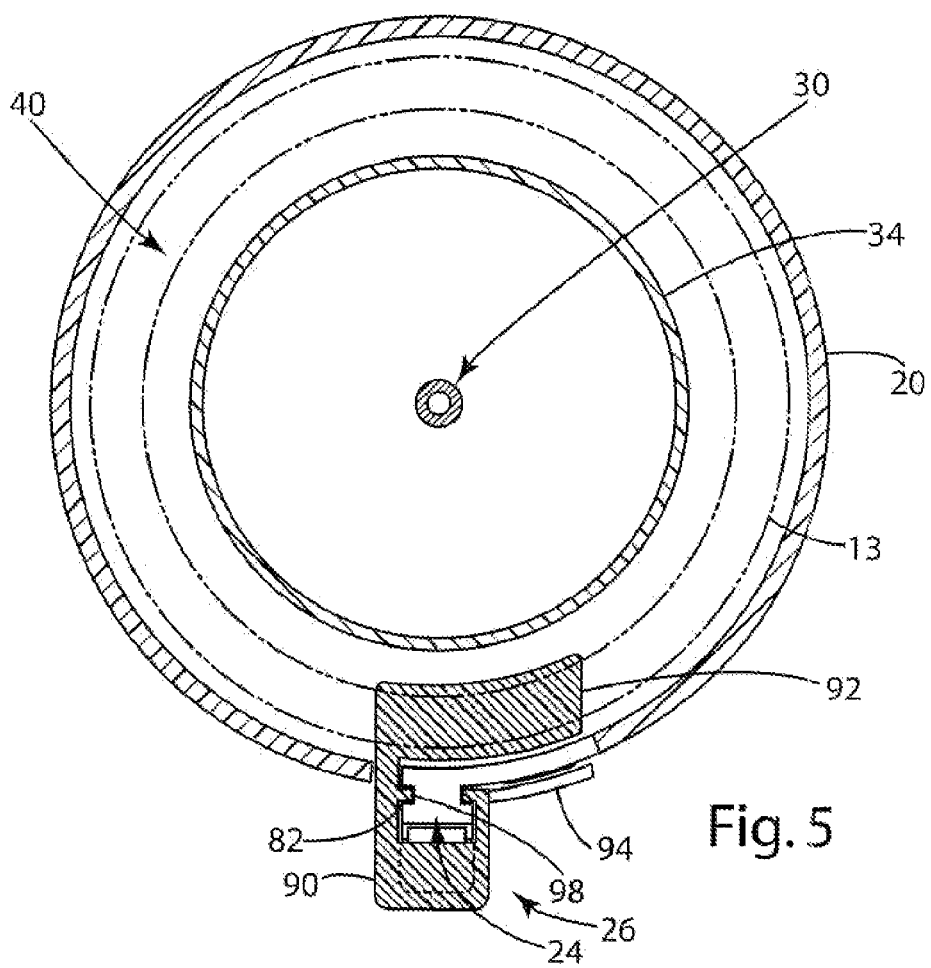
FIG. 5 is a sectional top view of the dosage control syringe.
Figure 6:
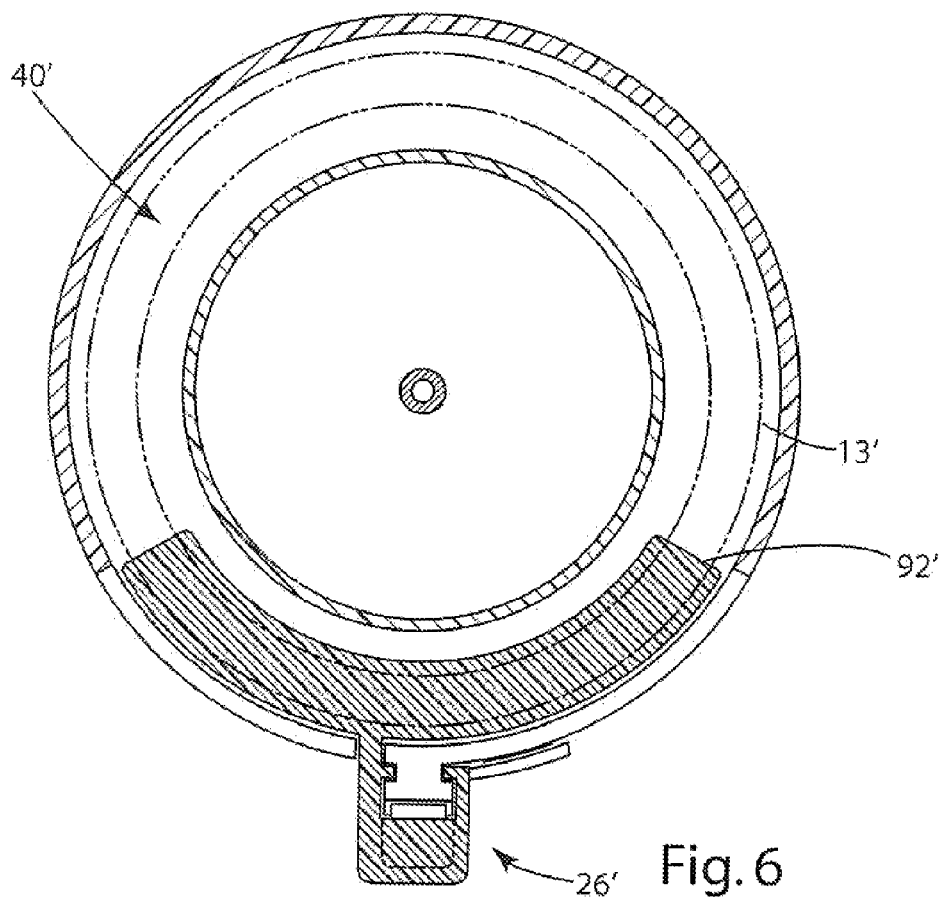
FIG. 6 is a sectional top view of an alternative embodiment of the dosage control syringe.

As shown at least in FIG. 5, the track 24 includes two side channels which act as a guide 82 for the dosage control 26. Although FIGS. 5 and 6 depict two separate embodiments each with two side channels, alternative embodiments may have additional, fewer, or no side channels. For example, in one embodiment the track 24 may only have a single side channel. In one embodiment, instead of channels, a substantially ring shaped portion of the dosage control 26 fits around and is guided by the support structure 34.

In the illustrated embodiments the track 24 is integrally formed with the exterior surface of the syringe barrel 20. The locking mechanism 80 is disposed along the length of the track 24 as a ratchet bar with a plurality of sloping teeth. Although the illustrated locking mechanism 80 is implemented as a ratchet bar, alternative track constructions are contemplated which provide a plurality of catch positions for the dosage control 26. In the illustrated embodiment, the ratchets correspond with the dosage markings 60 (also known as measuring indicia) on the syringe barrel 20 in a one to one fashion. In alternative embodiments, the dosage markings 60 may correlate with the ratchets differently. For example, multiple ratchets may occur between each dosage marking 60. Although the depicted embodiment includes a track 24 disposed on the exterior surface of the syringe barrel 20, the track 24 may be disposed on the inside of the syringe barrel 20 or alternatively disposed on the support structure 34. Where the locking mechanism 80 is disposed on the support structure 34, access to the locking mechanism may be provided to a user outside of the syringe barrel 20 with a pawl or other suitable mechanism. In some embodiments, such as the three alternative embodiments shown in FIGS. 7-9, an additional track 25, 25', 25", and slot 43, 43', 43" are included on the opposite side of the syringe barrel 20 for additional guidance and support. The additional track may or may not include a locking mechanism.

Figure 5A:
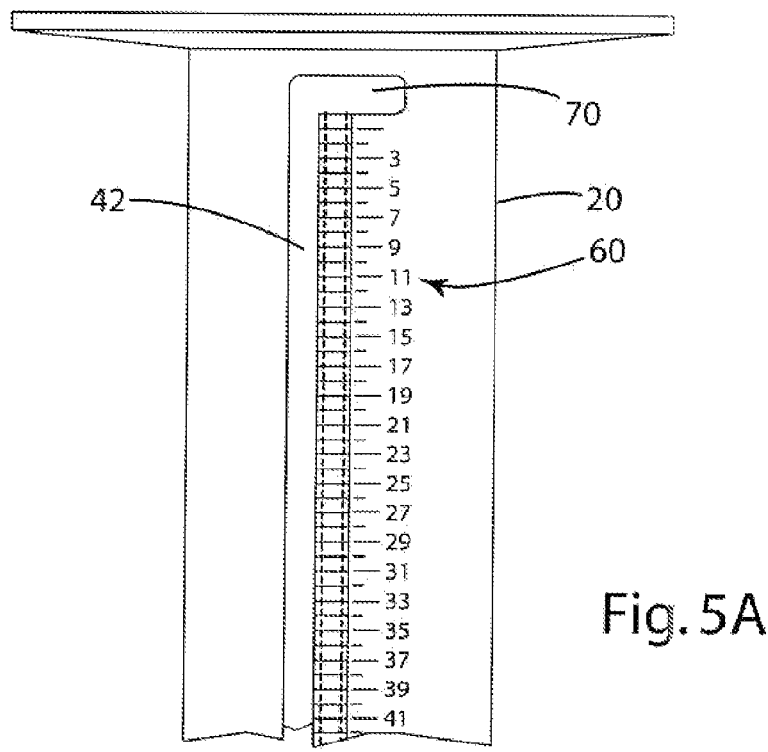
FIG. 5A is an orthogonal view of the dosage control syringe.
Figure 6A:
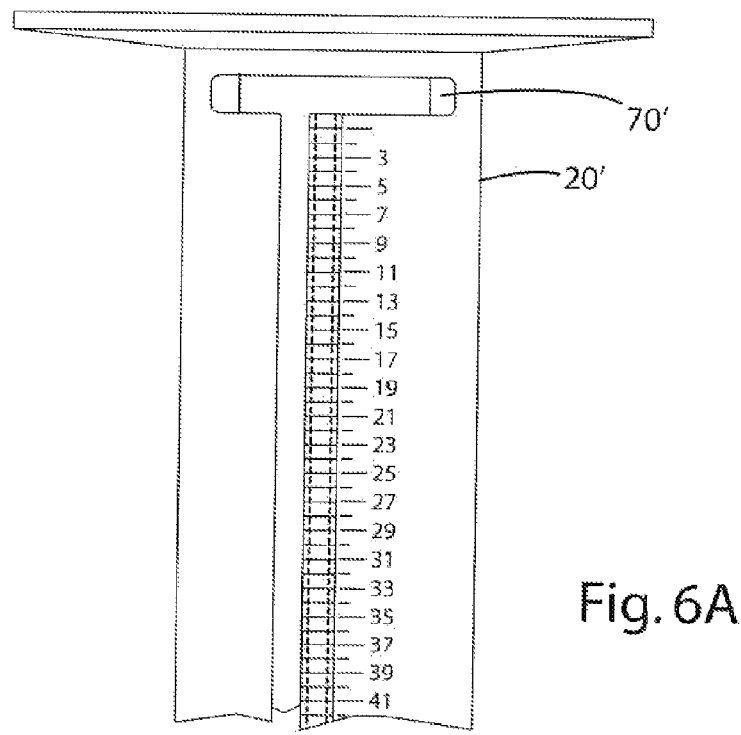
FIG. 6A is an orthogonal view of the dosage control syringe of FIG. 6.

The dosage control 26 is generally disposed on the track 24 before use. Specifically, in one embodiment, the dosage control 26 is inserted into the interior of the syringe barrel 20 through hole 70 and slid along slot 42 all the way to the bottom of the track 24. When the dosage control syringe is ready for use, the operator operates and slides the dosage control 26 to a desired position where the dosage control 26 may be locked. Although the dosage control 26 need not be prepared in this manner, pre-setting the dosage control 26 at the bottom of the track 24 allows an operator to quickly slide the dosage control 26 from the bottom to a desired location quickly without having to find and insert a dosage controls. FIG. 5A depicts that the size of the hole 70 is large enough for the dosages control 26 to be inserted into the syringe barrel. FIGS. 6 and 6A depict an alternative embodiment where the hole 70' is large enough for the larger, dosage control 26' to be inserted inside the syringe barrel 20'.

One embodiment of the dosage control 26 includes a slidable portion 90, a lockable obstruction 92 (also referred to as an "obstruction portion" of the dosage control 26), and a dosage indicator 94. These components need not be separate from one another. For example, in an alternative embodiment, the slidable portion may also function as a dosage indicator.

In one embodiment, the slidable portion 90 includes a pawl 96 to interface the locking mechanism 80 of the track 24 and two flanges 98 to interface the guide 82 of the track 24. The pawl 96 and flanges 98 may be replaced by other selectively lockable elements or a different selectively lockable system.

In the depicted embodiment, the pawl 96 engages any of the sloping teeth of the ratchet bar locking mechanism 80 to lock the entire dosage control 26, including the obstruction portion 92, into position. The pawl 96 acts as a locking mechanism to secure the entire dosage control 26 in position while it is locked. The pawl 96 has an end that may be operated by a user to disengage from the track 24 and change the pawl position. When the user releases the end, the pawl 96 reengages the track 24 and locks the dosage control 26 in position.

In the depicted embodiment, the flanges 98 provide a friction fit with the guide 82. In an alternative embodiment instead of a friction fit, the flanges 98 are shepherded into position by the guide 82.

The lockable obstruction 92 limits vial 12 movement within the barrel 14. The obstruction 92 may be essentially any size and shape which will limit vial 12 movement within the syringe barrel 20. A ring-shaped void 40 exists between the syringe barrel 20 and the support structure 34. The vial edge 13 fits within the void 10. FIG. 5 depicts one embodiment where the obstruction 92 is substantially rectangular to block a sufficient portion of the void 40 and obstruct the vial edge 13 upon engagement. FIG. 6 depicts an alternative embodiment, where the obstruction 92' substantially form-fits within and fills approximately one-third of the void 40'. The obstruction 92' of FIG. 6 blocks a sufficient portion of the void 40' to obstruct the vial edge 13' upon engagement.

Figure 7:
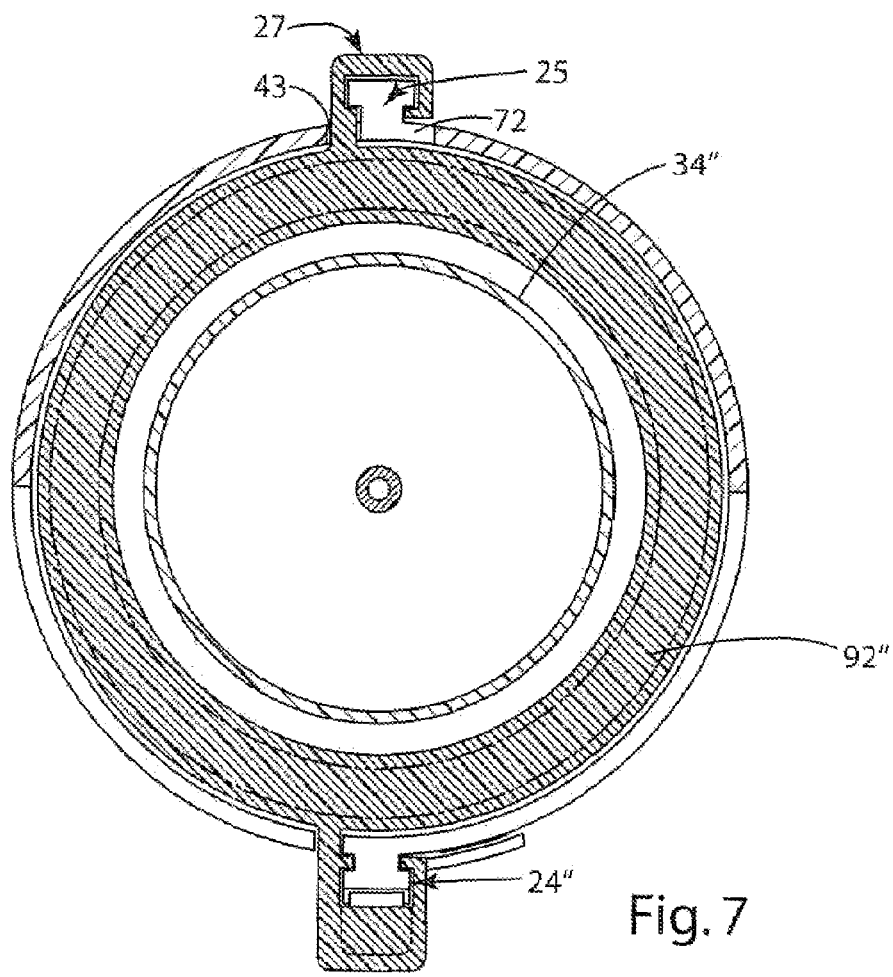
FIG. 7 is a sectional top view of another alternative embodiment of the dosage control syringe.
Figure 8:
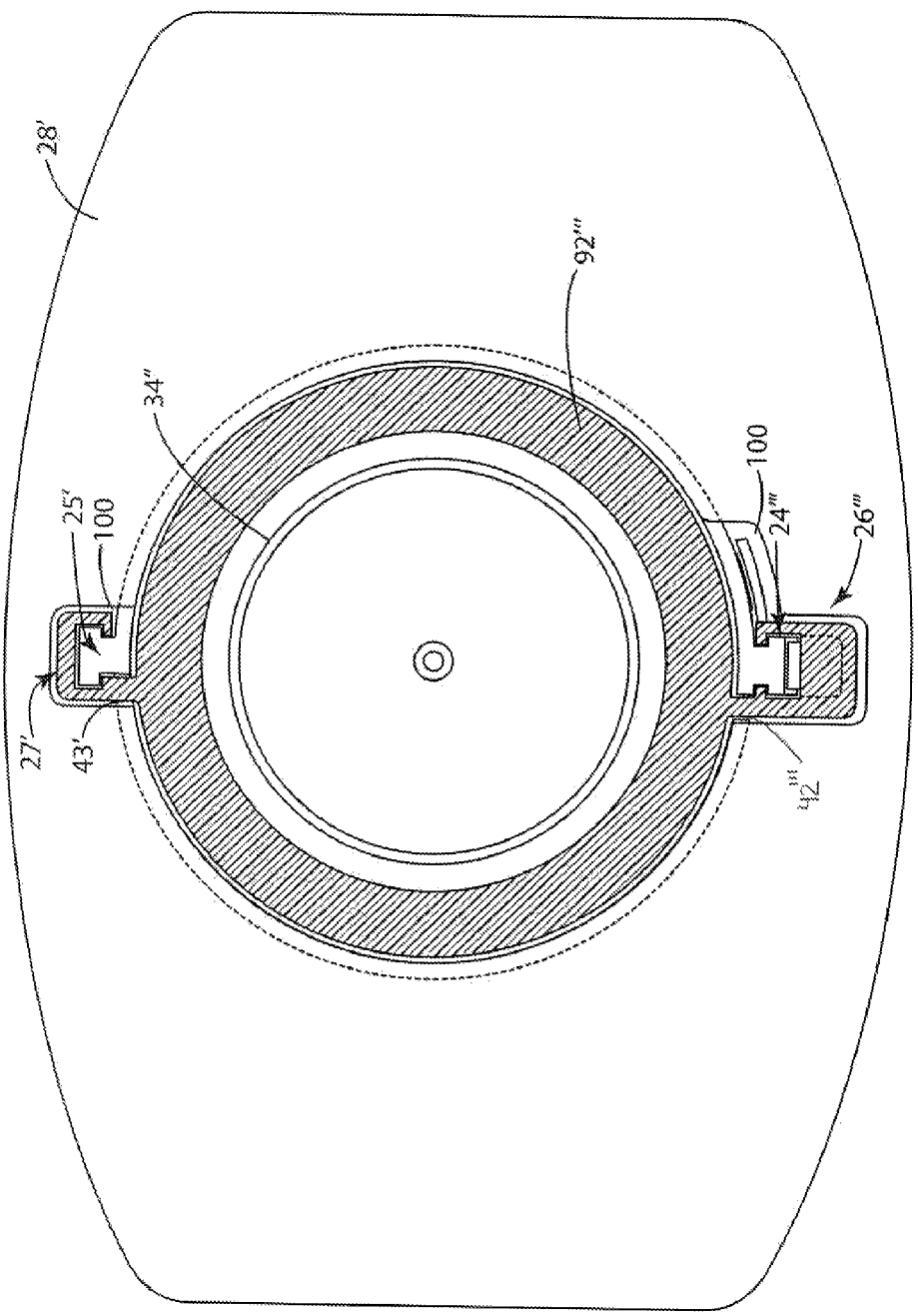
FIG. 8 is a top view of another alternative embodiment of the dosage control syringe.
Figure 9:
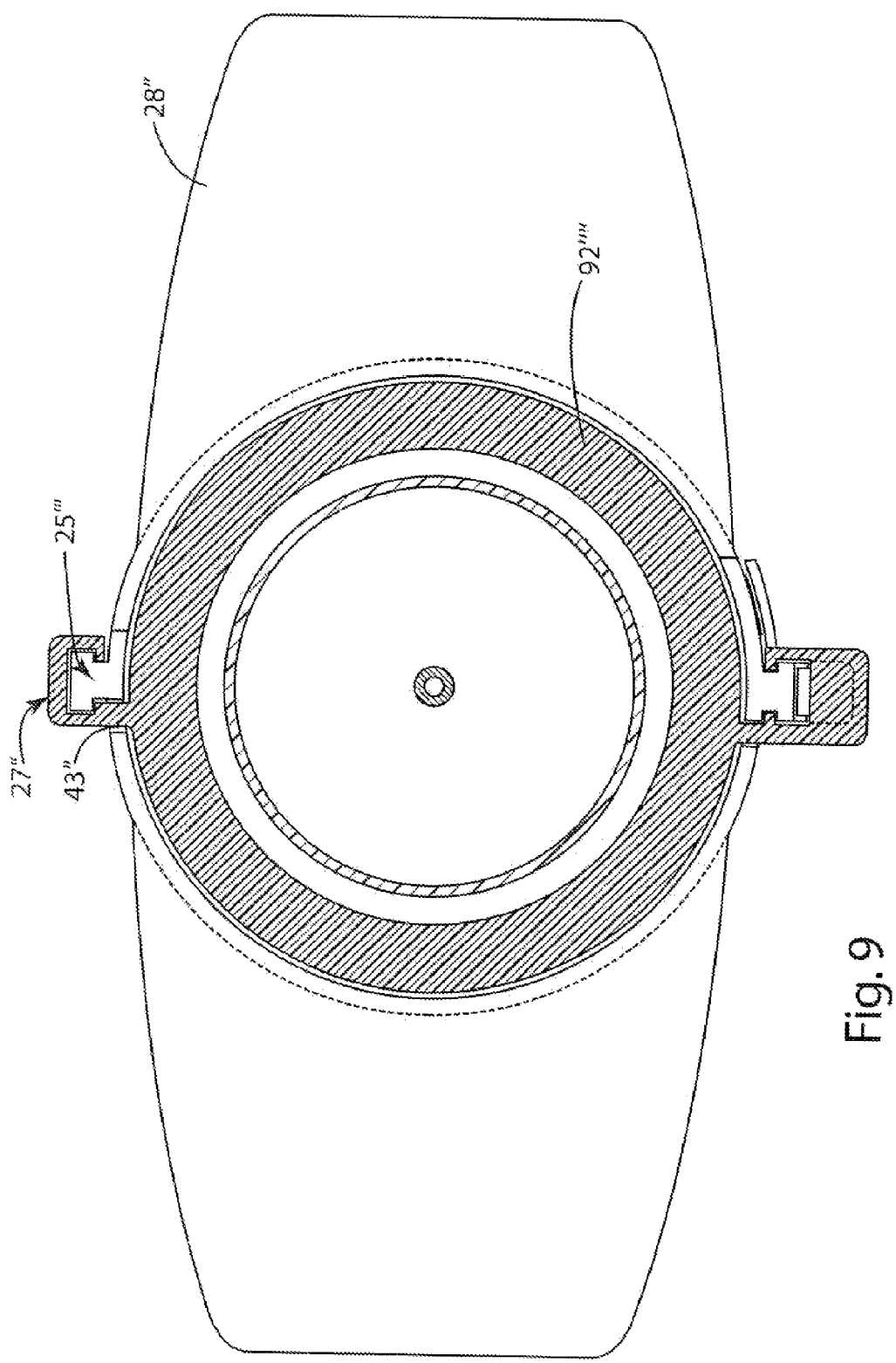
FIG. 9 is a top view of another alternative embodiment of the dosage control syringe.

In the two-track embodiments, FIG. 7-9, an additional dosage control or obstruction guide 27, 27', 27" may be provided which cooperates with the additional track 25, 25', 25". The two dosage controls may share a common circumferential (i.e. ring shaped) obstruction 92", 92''', 92''''. In the embodiment shown in FIGS. 7-9, the circumferential obstruction is sized with an outer circumference similar to the circumference of the syringe barrel 20.

Figure 7A:
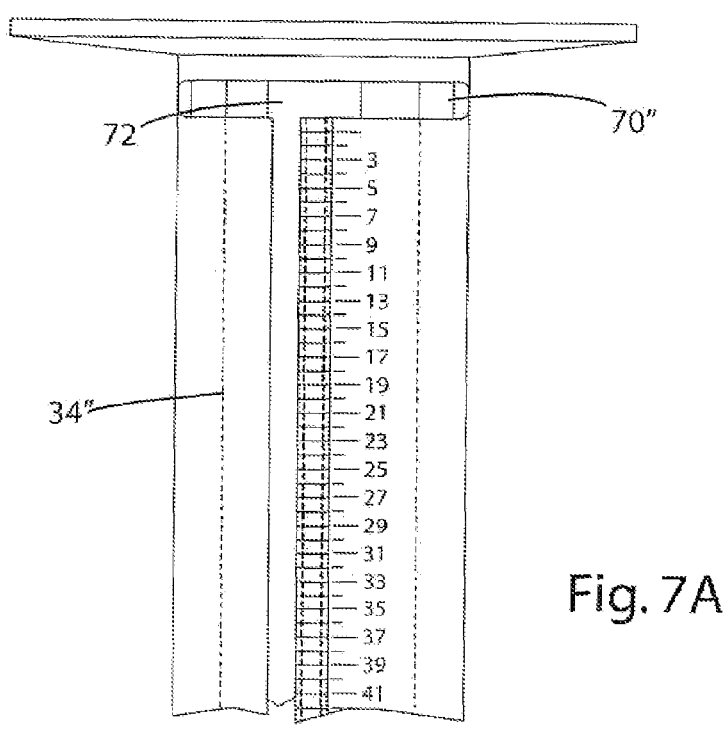
FIG. 7A is an orthogonal view of the dosage control syringe of FIG. 7.

Installation of the obstruction may be facilitated with a variety of syringe constructions. In one embodiment, shown in FIGS. 7 and 7A, the hole 70" is enlarged to approximately half the circumference of the syringe barrel so the obstruction 92" may be inserted through the side of the barrel 20. Further, a separate hole 72 on the syringe barrel 20, opposite hole 70", is included to facilitate installing the obstruction guide 27. Once the obstruction 92" is inserted it may be lowered along the tracks 24", 25 such that the obstruction 92" surrounds the support structure 34".

In another embodiment for inserting a dosage control 26''' into the barrel and onto the track 24''', shown in FIG. 8, the syringe barrel does not include holes to facilitate inserting the obstruction through the side of the barrel. Instead, the slots 42''', 43' extend to the top of the syringe barrel so that the obstruction 92''' may be inserted from the top of the syringe barrel. In this embodiment, The wings 28' include holes 100 large enough to facilitate top insertion. In another top insertion embodiment, shown in FIG. 9, the syringe includes two separate wings 28" such that no holes need be included in the wings 28".

FIG. 1 is a perspective view of one embodiment of a dosage control syringe in use. FIGS. 3-4 show how the vial 12 engages the injector assembly 14 when the syringe is in use. The syringe assembly 10 operates by selecting a dosage with the dosage control 26 to position the obstruction 92 within the injector assembly 14. The vial stopper 18 engages the needle assembly 22 to administer the vial contents 16 through the needle 30. As the vial 12 is pressured into the injector assembly 14 the stopper 18 remains fixed reducing tie vial volume and forcing the vial contents 16 into the needle assembly 22. The vial 12 may be pressured until the obstruction 92 engages with the vial edge 13. Applying further pressure once the vial 12 has engaged the obstruction 92 will not result in further substantial vial movement. Accordingly, the dosage control 26 selectively limits vial movement within the injector assembly 14 and therefore selectively limits dosage.

Once a specific medical solution in a vial is selected for injection or infusion, the vial stopper 18 is threadingly engaged with the rear end of the injector assembly 14, as shown in FIG. 3. Specifically, the vial stopper 18 is threadingly engaged with the threaded support structure 34 of the needle assembly 22. The vial stopper 18 is pierced by the needle so as to provide fluid communication to the proximal end of the needle.

Once fluid communication between the vial and needle is established, the vial may slide deeper into the syringe barrel 20 while the threaded vial stopper 18 stays fixed. As the volume inside of the vial decreases, medication 16 is forced through the needle from inside the vial. Vial movement is stopped once the vial 12 engages the dosage control obstruction 92, is shown in FIG. 4. Additional pressure will not substantially move the vial, and the dose is effectively, limited to the amount indicated by the dosage control indicator.

The above description is that of the current embodiment of the invention. Various alterations and changes can be made without departing from the spirit and broader aspects of the invention as defined in the appended claims, which are to be interpreted in accordance with the principles of patent law including the doctrine of equivalents. Any reference to claim elements in the singular, for example, using the articles "a," "an," "the" or "said," is not to be construed as limiting the element to the singular.

The invention claimed is:

1. A syringe comprising:
a syringe barrel including a slot;
a needle mounted at least partially within the syringe barrel;
a vial closed with a stopper for interfacing the needle, where the vial is slidable within the syringe barrel and the stopper is substantially unmovable relative to the syringe barrel;
a track disposed on the syringe; and
a lockable obstruction positioned through the slot moveable along the track to selectively limit vial movement within the syringe barrel and therefore selectively limit dosage, where the syringe barrel includes measuring indicia and the lockable obstruction includes an indicator for use with the indicia.

2. The syringe of claim 1 where the indicia are indicative of weight.

3. The syringe of claim 2 where the syringe barrel includes an aperture to facilitate an initial interface between the lockable obstruction and the track.

4. A syringe comprising:
a syringe barrel including a slot;
a needle mounted at least partially within the syringe barrel;
a vial closed with a stopper for interfacing the needle, where the vial is slidable within the syringe barrel and the stopper is substantially unmovable relative to the syringe barrel;
a track disposed on the syringe; and
a lockable obstruction positioned through the slot moveable along the track to selectively limit vial movement within the syringe barrel and therefore selectively limit dosage, where the track comprises a ratchet bar and the lockable obstruction comprises a pawl.

5. A syringe comprising:
a syringe barrel including a slot;
a needle mounted at least partially within the syringe barrel;
a vial closed with a stopper for interfacing the needle, where the vial is slidable within the syringe barrel and the stopper is substantially unmovable relative to the syringe barrel;
a track disposed on the syringe; and
a lockable obstruction positioned through the slot moveable along the track to selectively limit vial movement within the syringe barrel and therefore selectively limit dosage, where the lockable obstruction comprises a ring sized with an outer circumference similar to a circumference of the syringe barrel.

6. The syringe of claim 5 further including a second track, and second slot, where the lockable obstruction is positioned through the second slot moveable along the second track.

7. The syringe of claim 5 where the lockable obstruction comprises:
a pawl portion for interfacing the track outside the barrel; and
a portion for obstructing the vial inside the barrel.

8. A syringe comprising:
a syringe barrel including a slot;
a needle mounted at least partially within the syringe barrel;
a vial closed with a stopper for interfacing the needle, where the vial is slidable within the syringe barrel and the stopper is substantially unmovable relative to the syringe barrel;
a track disposed on the syringe; and
a lockable obstruction positioned through the slot moveable along the track to selectively limit vial movement within the syringe barrel and therefore selectively limit dosage, where the lockable obstruction comprises:
a pawl portion for interfacing the track outside the barrel; and
a portion for obstructing the vial inside the barrel, where the portion for obstructing the vial inside the barrel comprises approximately one-third of a substantially planar ring inside the syringe barrel.

9. The syringe of claim 8 further including a threaded support structure, where the needle is mounted on the support structure and where the vial is only slidable within the syringe barrel if the vial is mateable with the threaded support structure.

10. A syringe comprising:
an elongated hollow barrel having a first end, a second end, and a length between;
a needle mounted at least partially within the barrel through the first end;
a vial with a stopper for engaging the needle, the vial being movable through the second end along the length inside of the barrel;
a track disposed along a portion of the length of the barrel; and
an adjustable dosage control comprising
a locking mechanism selectably slidable along the track for indicating a dosage;
an obstruction inside the barrel in communication with the locking mechanism for limiting vial movement to provide the indicated dosage.

11. The syringe of claim 10 where the obstruction comprises a portion of the inside of the barrel sufficient to substantially impede the vial from sliding in one direction of the barrel when the syringe is in use.

12. The syringe of claim 10 where the barrel includes measuring indicia and the locking mechanism includes an indicator for use with the indicia.

13. The syringe of claim 12 where the indicia are indicative of weight.

14. The syringe of claim 10 where the barrel includes an aperture to facilitate inserting the obstruction inside the barrel.

15. The syringe of claim 10 where the track comprises a ratchet bar and the locking mechanism comprises a pawl.

16. The syringe of claim 10 where the obstruction comprises approximately one-third of a substantially planar ring inside the syringe barrel.

* * * * *